United States Patent
Le Comte (10) Patent No.: US 9,952,238 B2
(45) Date of Patent: Apr. 24, 2018

(54) AUTOMATIC METHOD OF PREPARING SAMPLES OF TOTAL BLOOD FOR ANALYSIS, AND AN AUTOMATIC DEVICE FOR IMPLEMENTING THE METHOD

(75) Inventor: Roger Le Comte, Perols (FR)

(73) Assignee: Horiba ABX SAS, Montpellier (FR)

( * ) Notice: Subject to any disclaimer, the term of this patent is extended or adjusted under 35 U.S.C. 154(b) by 1859 days.

(21) Appl. No.: 11/994,959

(22) PCT Filed: Jul. 4, 2006

(86) PCT No.: PCT/FR2006/001583
§ 371 (c)(1),
(2), (4) Date: Jan. 7, 2008

(87) PCT Pub. No.: WO2007/006903
PCT Pub. Date: Jan. 18, 2007

(65) Prior Publication Data
US 2009/0142844 A1    Jun. 4, 2009

(30) Foreign Application Priority Data

Jul. 8, 2005  (FR) ...................................... 05 07341

(51) Int. Cl.
*G01N 35/00* (2006.01)
*G01N 35/04* (2006.01)
*G01N 35/10* (2006.01)

(52) U.S. Cl.
CPC ... *G01N 35/00594* (2013.01); *G01N 35/0092* (2013.01); *G01N 35/0099* (2013.01);
(Continued)

(58) Field of Classification Search
CPC . G01N 2035/00524; G01N 2035/0093; G01N 2035/0092; G01N 35/0099; G01N 35/00584; G01N 35/0092
(Continued)

(56) References Cited

U.S. PATENT DOCUMENTS 4,873,663 A    10/1989 Baranyai et al.
4,921,676 A *  5/1990 Otani ............................ 422/510
(Continued)

FOREIGN PATENT DOCUMENTS

EP         0 344 819 A1    12/1989
WO   WO 2005/019835      *  3/2005  ............. G01N 35/00

*Primary Examiner* — Jonathan M Hurst
(74) *Attorney, Agent, or Firm* — Fitch, Even, Tabin & Flannery, LLP (57) ABSTRACT

The present invention relates to a method of preparing analyses of total blood samples and to a device that is useful for implementing the method, said samples being conserved in tubes including at least one identification means for identifying the sample, the device comprising:

at least one compartment constituting a said storage zone for storing said tubes before and after analysis; and at least one said read means for reading said identification means of said tubes; and at least one preparation zone for preparing said blood samples prior to analysis and including means for verifying and/or treating said tubes containing said samples, and in particular at least one agitator means for agitating said tubes; and at least one access zone giving access to at least one automatic analyzer of total blood, said access zone enabling a said tube to be placed in said analyzer; and robotic gripper and displacement means controlled by an automatic controller and suitable for taking hold of and replacing said tubes individually in said storage zone and for conveying them in at least three directions XYZ between said storage zone, said preparation zone and said access zone giving access to said analyzer, said analyzer preferably being connected to and/or controlled by said automatic controller.

25 Claims, 4 Drawing Sheets

(52) U.S. Cl.
CPC ....... *G01N 35/00584* (2013.01); *G01N 35/04* (2013.01); *G01N 35/1097* (2013.01); *G01N 35/00712* (2013.01); *G01N 2035/00524* (2013.01); *G01N 2035/0406* (2013.01); *Y10T 436/10* (2015.01); *Y10T 436/114165* (2015.01)

(58) Field of Classification Search
USPC .............................................. 436/47; 422/64
See application file for complete search history.

(56) References Cited

U.S. PATENT DOCUMENTS

| | | | |
|---|---|---|---|
| 4,927,545 | A | 5/1990 | Roginski |
| 5,437,985 | A * | 8/1995 | Quintana et al. ............ 435/7.24 |
| 5,646,046 | A | 7/1997 | Fischer et al. |
| 5,885,530 | A * | 3/1999 | Babson et al. .................. 422/65 |
| 6,060,022 | A * | 5/2000 | Pang et al. ...................... 422/65 |
| 6,080,364 | A * | 6/2000 | Mimura et al. ................. 422/67 |
| 6,114,292 | A * | 9/2000 | Hoshiko et al. ............... 510/161 |
| 6,586,255 | B1 * | 7/2003 | Hubert et al. .................. 436/45 |
| 6,787,361 | B1 * | 9/2004 | Klee ................................. 436/8 |
| 8,029,732 | B2 * | 10/2011 | Le Comte ....................... 422/73 |
| 2002/0001542 | A1 | 1/2002 | Itoh |
| 2002/0021983 | A1 | 2/2002 | Comte et al. |
| 2004/0037680 | A1 * | 2/2004 | Sato .................... B65G 1/0435 414/281 |
| 2004/0121484 | A1 * | 6/2004 | Betancourt et al. .......... 436/174 |
| 2004/0185549 | A1 * | 9/2004 | Fujita et al. ............... 435/287.2 |
| 2005/0249634 | A1 * | 11/2005 | Devlin, Sr. ..................... 422/64 |
| 2006/0210435 | A1 * | 9/2006 | Alavie et al. .................. 422/65 |

* cited by examiner

AUTOMATIC METHOD OF PREPARING SAMPLES OF TOTAL BLOOD FOR ANALYSIS, AND AN AUTOMATIC DEVICE FOR IMPLEMENTING THE METHOD

The present invention relates to a method of preparing samples of total blood in order to perform hematological analyses with the help of one or more automatic total blood analyzers, and the invention also relates to an automatic preparation device for implementing the method.

BACKGROUND OF THE INVENTION

Amongst other things, the invention seeks to define a protocol for automatically preparing samples of total blood for the purpose of improving the reliability of analyses performed using automatic analyzers, and also to improve the flexibility with which such analyses can be implemented with the help of such automatic analyzers.

Blood analyses performed on total blood (hematological analyses) are performed on tubes of blood that contain all of the components of blood, unlike analyses that are performed on blood serum or plasma, as obtained after coagulating or centrifuging samples of blood taken from patients.

In order to be carried out properly, such analyses on total blood require sustained agitation of the tubes of blood for analysis in order to thoroughly mix all of the components of the blood such as the platelets and the red and white corpuscles that are to be counted during analysis. This agitation stage is essential for ensuring the quality of the analyses and it must be carried out very shortly before analysis and in compliance with criteria that are standardized.

Tubes of blood for analysis are identified by bar codes giving access to information relating to the patients and also to the analyses that are to be performed on the samples of blood contained in the tubes.

These tubes are sorted by category and they are placed on supports, commonly referred to as racks, that are suitable for receiving a plurality of tubes. After prior agitation they can then be introduced manually and individually into an automatic analyzer. The tubes can also be placed in cassettes or racks that are specific to each analyzer and that have about ten housings in alignment, in which the tubes are placed and generally secured manually by an operator, who then places said cassettes or racks in a loading compartment of the analyzer.

Said cassettes are then taken in charge automatically by the analyzer, which then performs the operations of conveying, agitating the tubes, analyzing the samples of blood contained in each of the tubes, and finally storing said cassettes once all of the tubes of blood placed thereon have been analyzed.

Such automatic analyzers suitable for taking charge of cassettes or racks carrying a plurality of tubes of blood for analysis are described in particular in the following documents : U.S. Pat. No. 4,609,017, EP-A-0 726 453, and EP-A-0 645 006.

The use of such automatic analyzers is nevertheless not entirely satisfactory. Regardless of the mode of analysis used, the operator needs to transfer each of the tubes manually from a rack into the analyzer or a cassette, and then after analysis the operator needs to extract the tubes from the analyzer or from said cassette in order to replace them on racks, so that they can be conserved for a short period in refrigerators in order to make it possible to analyze them again, should that be necessary in order to verify that the results of particular analyses are exact.

For each tube for analysis, the operator thus needs to take care to engage the tube of blood properly in the cassette, to turn it so as to make its bar code label visible to the reader so that it can be identified, and to avoid becoming contaminated with the blood.

Furthermore, when it is appropriate to verify a first result, it is difficult for the operator to identify amongst the set of tubes, which tube needs to be analyzed again. The operator needs to verify each of the bar code labels on the tubes in order to identify visually the tube containing the sample that needs to be verified, and then needs to reintroduce said tube individually into the analyzer (or else the entire cassette on which said tube is located), which can be particularly time consuming and lengthy to perform.

Implementing hematological analyses with the help of present analyzers thus lacks flexibility.

Automatic systems are also known for feeding tubes for analysis from a storage zone to an analysis point where they are taken into charge by one or more analyzers, as described in document U.S. Pat. No. 5,232,081. That comprises a system for conveying cassettes filled with tubes and placed on a rail that transports the cassettes from one analyzer to another, starting from a storage compartment, with the cassettes being put into place on the conveyor rail automatically as a function of the rate of throughput of the analyzers. Automatic systems of that type for feeding analyzers with tubes of blood do not solve the above-defined problems of flexibility in implementing analyses, even though they do enable them to be carried out at a faster rate.

In addition, conveying entire cassettes requires a conveyor system of large dimensions to be built so as to enable the direction of cassettes to be changed on the system, on curves of small radius, which makes the use of such cassette conveyor systems particularly inconvenient and difficult in laboratories.

Document EP-A-0 344 819 describes a device serving essentially to store and mix tubes of blood for analysis. The device makes provision only for agitating the tubes and not for any other step in preparing samples. Each tube is placed on an individual support in a storage zone and then the tubes are moved in succession one by one by a mechanism that is very complex and bulky to the agitator device and to a zone giving access to an analyzer.

Although automatic, that device suffers from the same drawbacks as analysis devices using cassettes. It is necessary for the operators to introduce the tubes one by one into their supports in the storage compartment. In addition, its operation does not provide any flexibility in the order in which tubes are prepared and analyzed.

Better flexibility is obtained by a device of the kind described in document U.S. Pat. No. 4,927,545. That document describes a device for automatically treating blood serum, the device comprising a computerized control unit driving a 5-axis robot arm that handles tubes of blood serum between various apparatuses. Nevertheless, that device is very bulky which makes it unsuitable for use in laboratories where a very large number of analyses need to be performed every day and where a large number of operators work and move about. In addition, the device of U.S. Pat. No. 4,927,545 is unsuitable for treating samples of total blood, insofar as it does not enable tubes to be prepared individually in automatic manner.

Another drawback of existing automatic analyzers and automated feeder systems lies in the fact that they are not suitable for coping with emergency situations of the kind commonly encountered in analysis laboratories. In such emergency situations, it is essential for an operator to be able to carry out an analysis on a tube of blood that is not in the analyzer or on the feed system of the analyzer, so as to be able to obtain results immediately. To do this, the operator is obliged to stop the analyses that are in progress, in order to introduce the tube for emergency analysis into a cassette ready for entering the analyzer and taking the place of one of the tubes to be found therein. Thereafter, once the emergency analysis has been carried out, the normal analysis process that was stopped needs to be restarted. That likewise represents operations that are constraining and lengthy for the operator and also leads to untimely stoppages in the process of routine analyses, thus interfering with the reliability of the analyses performed and thus in the accuracy of the results provided.

The device described in EP-A-0 344 819 is unsuitable, in particular, for coping with such emergency situations.

Finally, before beginning to analyze tubes of blood, operators need every day to perform quality control operations on analyzers, by analyzing tubes containing control samples of blood for which the various parameters have known values with known tolerances relative to said values, in order to verify that the measurements performed by the analyzer are exact, and where appropriate in order to adjust the analyzer in suitable manner so that it will subsequently perform correct analyses on unknown samples. With certain national legislations, it is necessary to perform such quality control operations several times a day in order to be certain that the analyzers do not drift out of adjustment during the day and that the quality of the analyses remains constant at all times.

Tubes containing control samples of blood need to be stored in refrigerators while they are not in use, so that for each quality control operation, operators must stop the analyzer, then take an appropriate control sample tube from a refrigerator, verify that the tube is indeed appropriate for the operation that is to be performed, and in particular that the blood in the control sample has not reached its use-by date and has not already been subjected to too great a number of analyses. Thereafter, it is necessary to allow the control sample tube to return to room temperature and then to perform quality control operations by analyzing the control sample in compliance with the standards in force, and finally, once quality control is finished, the tubes must be put back into the refrigerator, after which normal analyses can be restarted.

There also, the operations of performing quality control on analyzers are particularly lengthy and laborious for operators to implement, and it can happen they do not give sufficient care to complying with the conditions under which tubes of control sample blood need to be conserved and used.

OBJECTS AND SUMMARY OF THE INVENTION

An object of the present invention is thus to provide a method of preparing samples of total blood for analysis that enables an automatic analyzer to be fed with said samples, while avoiding the drawbacks associated with using present automatic analyzers.

In particular, the present invention seeks to provide a method of preparation that enables implementing hematological analyses to be more flexible, in particular by making it easier to manage emergency analyses.

An object of the invention is also to propose a method of preparing analyses, in particular of samples of total blood, that can solve problems associated with the operations of performing quality control on analyzers.

Another object of the invention is to propose a method that enables the reliability of the analyses that are performed to be improved, in particular by ensuring that the tubes containing samples for analysis are properly conditioned, while also managing in autonomous manner the stages of performing quality control on the analyzer and adjusting it accordingly.

The invention also seeks to provide a device that is dedicated to preparing samples of total blood for analysis in accordance with the method of the invention.

Thus, in a first aspect, the invention achieves these objects by a method of preparing samples of total blood for analysis, said samples being conserved in tubes including sample-identification means and that are preferably hermetically closed by respective plugs, the method being characterized by the following steps in succession:

a) placing a said tube in a storage zone and identifying it by reading its said identification means with the help of suitable read means and recording the information as read in an automatic controller in order to know the identity of the patient and the type of analysis to be performed on the blood sample contained in said tube; and b) individually taking and moving each of said tubes with the help of robotic gripper and displacement means under the control of said controller, from said storage zone to at least one zone for preparing the tube and the sample of blood; and c) preparing said tube and said sample in said preparation zone in application of a preparation sequence that is determined as a function of information read from on said sample identification means and/or on the basis of information input into said automatic controller by an operator, said sequence including at least agitating the tube so as to mix together the components of the blood contained therein; and d) immediately after its preparation, individually moving said tube with the help of said robotic gripper and displacement means to at least one access zone giving access to an automatic analyzer of total blood in order to analyze the blood sample contained in said tube; and e) extracting said tube from said analyzer via a said access zone after analysis and replacing it in said storage zone with the help of said robotic gripper and displacement means; and preferably f) reiterating operations a) to e) on other samples.

In accordance with a preferred characteristic of the method of the invention, in step a) said tubes are placed and held vertically in supports, each comprising a plurality of individual housings of format suitable for receiving a tube and organized in a plurality of rows of adjacent housings, said supports being positioned in a said storage zone suitable for receiving a plurality of said supports and accessible by said robotic gripper and displacement means.

In order to ensure that the blood samples are analyzed under good conditions, it is also appropriate to ensure that no element disturbs the operations whereby the automatic analyzer takes blood from the tube. That is why in step c) is preferable to perform at least one of the following additional preparation operations:

causing aeration of the tube; and
verifying the level of said sample of blood in said tube; and
determining whether any clots exist in the sample contained in said tube; and verifying the depth to which the plug closing said tube has been engaged.

In addition, in some circumstances it is also possible in step c) also to bring said sample to temperature, preferably by heating it.

According to another preferred characteristic of the method of the invention, in step e), the tubes are sorted and stored in different ones of said supports with the help of said robotic gripper and displacement means and as a function of the results of analyses performed on the samples contained in said tubes, or as a function of optimizing space in the racks, or indeed as a function of additional analyses that are to be performed on said samples.

In accordance with the national legislation in force in most countries, it is required to verify the accuracy of automatic analyzers every day before proceeding with analyses of unknown blood samples. That is why in accordance with the invention, prior to preparing and analyzing said samples of total blood, control samples of blood are used for performing quality control on the analyzer, said control samples being conserved in a refrigerated zone that is accessible to said robotic gripper and displacement means, said control samples of blood being heated and prepared like samples of unknown total blood, and then introduced into said analyzer, and they are then automatically recovered and finally replaced in their starting locations in said refrigerated zone by said robotic gripper and displacement means.

Where appropriate, in order to satisfy the analysis standards in force in certain States and/or as applied in certain laboratories, the analysis of at least one control sample of blood is prepared periodically after a determined number of samples of total blood have been prepared and analyzed in a said analyzer, said control sample of blood being taken, prepared, delivered to the analyzer, and then recovered and stored by said robotic gripper and displacement means.

Thus, advantageously, during a day, spot checks are performed automatically to verify that the automatic analyzer used for analyzing blood has not drifted from its settings and still has sufficient accuracy and reliability to guarantee that the results of its analyses are valid.

In accordance with another advantageous characteristic, the method of the invention includes a protocol for automatically verifying the validity of the results of analyses performed by the automatic analyzers. For this purpose, and according to the invention, the following steps are performed:
  taking an average of each of the parameters analyzed on a series of a determined number of samples of unknown total blood; and
  comparing these mean values of the analyzed samples with ranges of nominal values for the same parameters, which nominal values correspond to healthy patients and are recorded in said automatic controller; and
  if one of said mean values lies outside the range of nominal values for the corresponding parameter, a control sample is prepared and the same parameter is analyzed on the control sample; and
  if the measured value for the analyzed parameter on the control sample lies in the range of nominal values for said parameter, analysis is continued on a new series of samples of unknown total blood samples; and
  if the value of the parameter analyzed on the control sample lies outside the range of nominal values for said parameter, then said analyzer is calibrated before analyzing a new series of samples of unknown total blood.

It is thus possible to detect any possible drift in the settings of the analyzer while performing analyses and to perform automatic verification (quality control) without any need for an operator to intervene, or to detect the presence of samples of pathological blood in a given series of samples when one or more mean values for the measured parameters lie outside the corresponding range(s) of nominal values.

In contrast, when the value of the parameter measured on the control sample lies outside the range of nominal values, then it is necessary to calibrate the analyzer, i.e. to correct the settings thereof, which calibration can be performed by an operator with the help of tubes of special calibration blood.

In a second aspect, the invention also provides an automatic device that is useful in preparing analyses of total blood samples using the method of the invention. The device comprising:
  at least one compartment constituting a said storage zone for storing said tubes before and after analysis; and
  at least one said read means for reading said identification means of said tubes; and
  at least one preparation zone for preparing said blood samples prior to analysis and including means for verifying and/or treating said tubes containing said samples, in particular at least one means for agitating said tubes; and
  at least one access zone giving access to at least one automatic analyzer of total blood, said access zone enabling a said tube to be placed in said analyzer; and
  robotic gripper and displacement means controlled by an automatic controller and suitable for taking hold of and replacing said tubes individually in said storage zone and for conveying them in at least three orthogonal XYZ directions between said storage zone, said preparation zone, and said zone giving access to said analyzer, said analyzer preferably being connected to and/or controlled by said automatic controller.

Advantageously, said device includes said supports having individual housings in which said tubes are placed by an operator, said supports being positioned in said storage zone and being manually removable therefrom, said storage zone being suitable for receiving a plurality of said supports and being accessible by said robotic gripper and displacement means to take tubes containing samples of total blood for analysis therefrom and for replacing the tubes therein.

In an advantageous embodiment, the device of the invention includes an emergency treatment compartment that is manually accessible to an operator from outside the device, said emergency treatment compartment also being accessible to said robotic gripper and displacement means and including at least one tube support element having at least one housing suitable for receiving a tube of blood.

The emergency treatment compartment enables a tube of blood to be inserted or withdrawn at any moment into or from the analysis system without it being necessary to stop the preparation device or the ongoing analyses, thereby facilitating preparation and analysis of tubes of blood for analyzing on a priority basis when said tubes are not already in the device.

According to a preferred characteristic, said verification and/or treatment means comprise one or more of the following
  at least one device for aerating said tubes; and/or
  at least one means for detecting the level of blood in a said tube and the presence of any clots in said blood; and/or
  at least one means for verifying the level to which the plugs are engaged in said tubes of blood; and/or
  at least one means for heating said tubes, preferably constituted by thermoelectrical cells.

In an advantageous embodiment, the preparation device of the invention includes a compartment for storing and conserving tubes containing control samples of blood that enable said analyzers to be verified, said compartment including means for cooling said tubes.

According to another preferred characteristic, said tubes of control samples are positioned and held in said conservation compartment in individual housings of a said support, said cooling means being constituted by thermoelectric cells (Peltier effect cells) preferably placed in said housings or on the peripheries thereof.

Integrating a compartment for storing control samples in the preparation device of the invention makes it possible advantageously to adapt the process of preparing tubes and of analyzing blood to the national regulations and/or internal procedures specific to analysis laboratories. With this disposition, all quality control operations, and in particular analyzer verification operations, can be performed automatically and rigorously without the operator needing to take charge of them in order to guarantee the security of results.

In accordance with another advantageous characteristic of the device of the invention, said robotic gripper and displacement means comprise an articulated clamp adapted to take hold of said tubes, preferably under the base of the plug, said clamp being movable vertically and horizontally in translation along three orthogonal XYZ axes by means of a transporter device having at least three guide rails directed along said XYZ axes and secured together in pairs, comprising a first rail that is horizontal and stationary, supporting a second rail that is horizontal and perpendicular to said first rail and that is movable in translation thereon, and a third rail that is vertical and secured to said second rail to be movable in translation thereon and perpendicularly thereto, said clamp being secured to said third rail.

In a particular embodiment of the robotic gripper and displacement means, they include an articulated arm provided at one of its ends with a gripper clamp for gripping said tubes of blood, e.g. of the multi-axis robot type.

To preserve the environment in which tubes of blood for analysis are handled and prepared together with the tubes of control samples of blood stored in the preparation device of the invention, and in order to protect all of the elements thereof together with the tubes of blood, in particular from impacts, vibration, and other external aggression, said preparation device is confined within a protective enclosure having at least a first opening giving access to at least one said analyzer and a second opening giving access to said emergency treatment compartment. In addition, such a protective enclosure also improves the safety of operators against any risk of splashing and/or malfunctioning of the device.

To make it easier to make the tubes of blood for analysis available to the analyzer from said preparation device, said analyzer access zone(s) advantageously comprise(s) a respective moving carriage suitable for moving between said device and a said analyzer, said carriage being controlled by said automatic controller and including at least one housing suitable for receiving a said tube of blood by said gripper and displacement means.

In a particular embodiment of the invention, said read means for reading said tube identifier means are secured to said robotic gripper and displacement means, and are preferably secured to said clamp.

In a particular embodiment of the invention, although controlled and directed directly by an automatic controller on the basis of an electronic map of the device as programmed and recorded in said automatic controller, said robotic gripper and displacement means also include means for detecting and/or viewing said tubes containing blood samples and said tubes containing said control samples of blood in said storage zones, said preparation zone, said analyzer access zone(s), said emergency treatment compartment, and said compartment for storing and conserving tubes containing control samples of blood.

These detection and/or viewing means advantageously make it possible to verify the presence of a tube in a determined location on the tube supports in the storage zone, in the emergency treatment compartment, or in the control sample tube conservation compartment, and also inform the control program when a location is empty so that it can be taken into account subsequently, or merely serve to adjust the alignment of the gripper clamp with the tube in order to ensure that the tube is taken hold of properly and is displaced properly within the device.

Where appropriate, in order to make it easier to store samples that have already been analyzed for the purpose of subsequent verification analysis, said supports placed in said storage zone and/or in said compartment for storing and conserving tubes containing control samples of blood also include identification means suitable for being read by appropriate read means.

The preparation device of the invention may also advantageously be coupled to an automatic analyzer so as to constitute a complete automatic analyzer system integrating all of the functions of preparing tubes for analysis, and of controlling the quality of the analyzer, said analyzer including means, in particular a needle, for taking blood from a sample for analysis contained in a tube that is hermetically closed by a plug and that is presented thereto from the preparation device via a said zone giving access thereto.

BRIEF DESCRIPTION OF THE DRAWINGS

Other characteristics of the invention appear on reading the following detailed description made by way of non-limiting example and with reference to the accompanying drawings, in which.

MORE DETAILED DESCRIPTION

Figure 1:
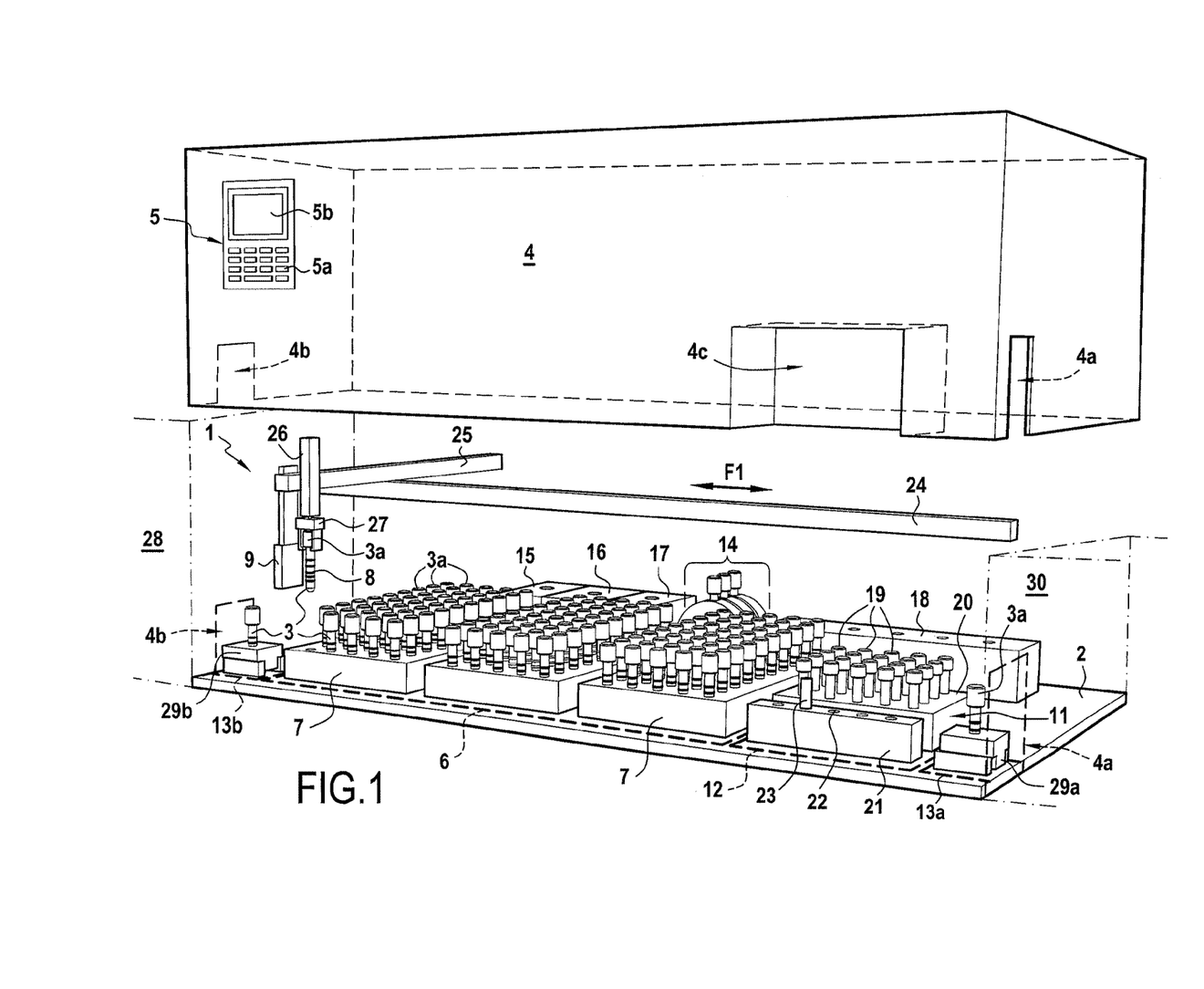
FIG. 1 is a diagrammatic perspective view of the device of the invention for preparing analyses of samples of total blood
Figure 2:
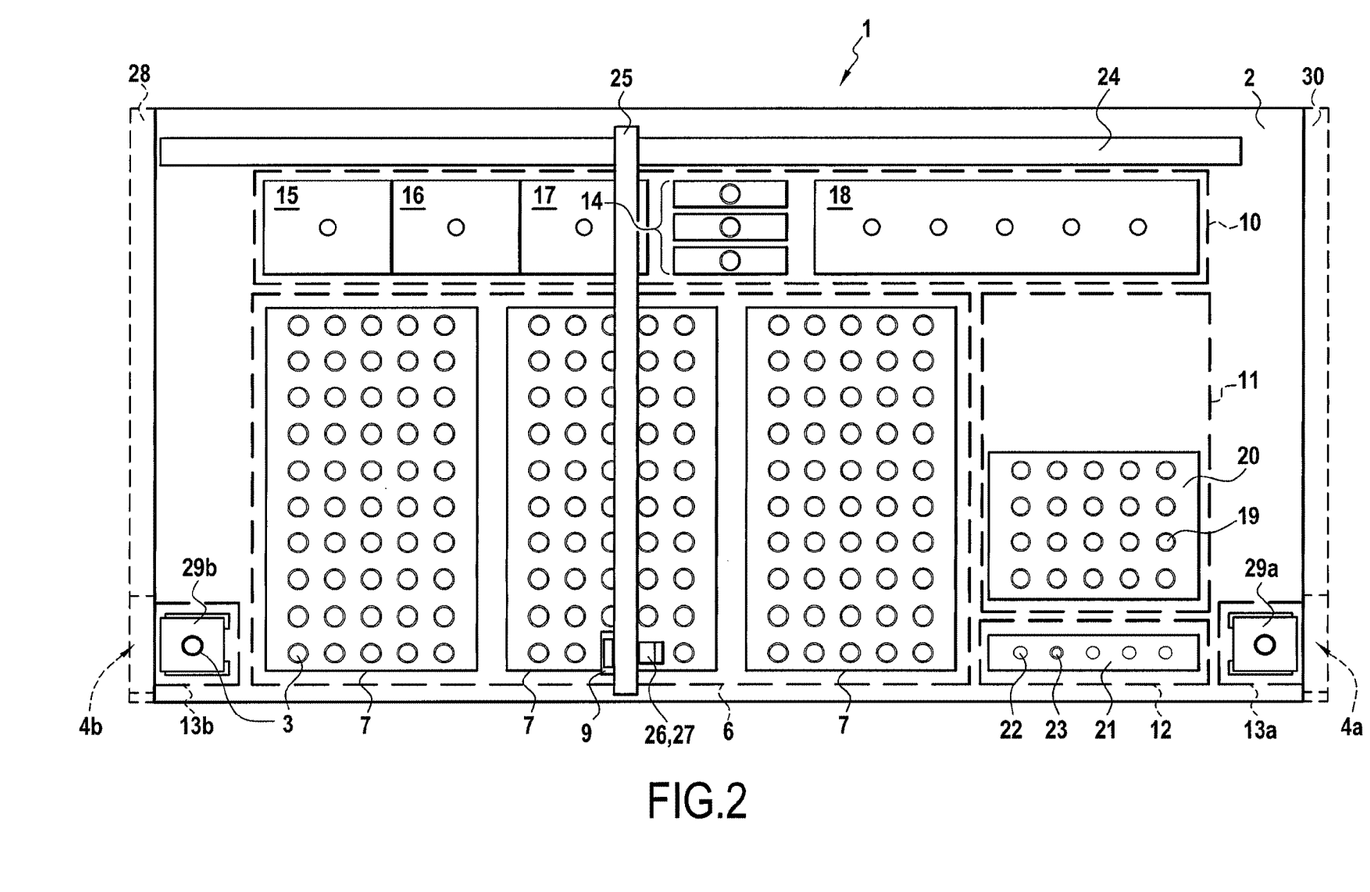
FIG. 2 shows the FIG. 1 device seen from above.

With reference initially to FIGS. 1 and 2, in the embodiment shown, the device 1 of the invention for preparing analyses of samples of total blood comprises a work surface 2 having a plurality of zones defined and distributed thereon for treating samples of blood contained in tubes 3, each having identification means 8 for identifying the sample contained therein, and each being hermetically closed by a plug 3a. The work surface 2 is covered by a protective and isolating enclosure 4 including openings 4a, 4b, and 4c giving access to certain zones of the device, and also including an automatic controller 5 for the device. Said automatic controller is connected to an input keyboard 5a and to a touch-sensitive screen 5b enabling an operator to communicate with the device via a man-machine interface.

In a variant embodiment, a computer that is auxiliary to the device and that is connected thereto could constitute said automatic controller in a manner well known to the person skilled in the art.

The tubes of blood 3 are to be analyzed by an automatic analyzer after being prepared for analysis in the device 1. In known manner, such an automatic analyzer includes means for taking blood that are suitable for piercing the plugs 3a of the tubes 3 in order to take therefrom a quantity of blood that is necessary and sufficient for the analyses that are to be performed or for making a smear of blood if the analyzer includes a slide spreader machine.

The device 1 for preparing analyses combines in a single common unit all of the means suitable for preparing tubes 3 of blood before they are introduced into the analyzer, in order to eliminate all of the time-consuming manual operations previously performed by operators for the purpose of preparing and implementing analyses on total blood, thus leaving them with more time for performing biological validation of the results.

For this purpose, the preparation device of the invention comprises on the work surface 2 a compartment that defines a storage zone 6 for storing tubes of blood to be analyzed, in which said tubes are placed on multiple-capacity supports 7 having a plurality of housings, in practice of the order of 25 to 100 housings depending on the dimensions of said supports. Said housings are of a format and a depth that are adapted to receiving and holding tubes 3 of blood in a vertical position. Such supports 7 are traditionally used in analysis laboratories for having tubes of blood placed therein and they are known as support racks.

The storage compartment 6 presents capacity that is variable as a function of the volume of analyses that are to be performed daily. In the example shown in the figures, it receives three racks 7, each having a capacity of about fifty tubes, however for laboratories of small to medium size, it might receive only one or two racks 7, or for laboratories of greater size and activity, or for hospitals, it might receive five or even more racks.

In order to provide even more modularity and adaptability, said storage compartment may advantageously be constituted in a particular embodiment by one or more drawers (not shown) that are pulled out for loading and unloading racks in the preparation device 1. The racks 7 also preferably include bonding means or fasteners (not shown) for engaging the bottom of the storage compartment, enabling them to be held in place during operations of manipulating the tubes 3, as described below.

Depending on circumstances, it is possible to introduce into the storage compartment 6 racks that are completely filled with tubes 3 for analysis, racks that are empty, or indeed racks that are filled in part only. Thus, when all of the racks 7 are full, each tube 3 is prepared by the device 1, and then inserted into an automatic analyzer for analysis, and then put back into place after the analysis in the storage compartment 7 in the housing of the rack 7 in which it was stored initially.

In contrast, if there are both full racks and empty racks in the storage compartment 6, then it is possible for the operator to set the device 1 via its said automatic controller 5 so that it takes tubes 3 from the full racks 7 and, after analysis, replaces them in the empty racks 7, either in random manner or after sorting them and grouping them together as a function of the results of the analyses on different racks that can subsequently be identified by an operator.

Finally, if racks 7 that are partially filled with tubes are reintroduced into the storage compartment, then at the request of the operator, the device enables the storage of the tubes in the racks to be optimized by grouping together tubes 3 at the end of analysis on a minimum number of racks, so as to economize on the number of racks used for storing tubes of blood, and consequently economize on the room occupied in the refrigerators where the tubes are stored for a day or two after being analyzed.

Advantageously, said racks are fitted with identification means 8a such as a radiofrequency identification marker, a magnetic label or strip, or a bar code, enabling information relating to the tubes 3 placed in the racks 7 to be read and/or written. The tubes 3 and the racks 7 identified in this way can be more easily recovered in the event of a request for a new analysis. The information can advantageously be read and recorded by a suitable reader 9a, such as a radiofrequency transponder or a bar code reader, that is movable within the storage compartment 6 in register with said identification means and that is connected to the automatic controller 5.

Similarly, each of the tubes 3 of blood likewise has identification means 8 for identifying the blood sample it contains. Said identification means may be constituted by a bar code or by a radiofrequency marker (RFID), for example, and it is read by means of a suitable reader 9 as soon as tubes have been placed in the storage compartment. This makes it possible to determine the position of each of the tubes in the storage compartment 6, and also makes it possible automatically to make a list of the tubes present in the device and of the analyses to which they are going to be subjected, thereby determining how each of the tubes should be prepared.

Although bar codes are traditionally used in the field of analyzing blood as in many other domains, radiofrequency identification (RFID) is a technique that is particularly suitable for storing and recovering data relating to blood samples. The markers used may in particular be adhesive labels 8, 8a that can be stuck on or incorporated in the tubes, and that can be read and updated automatically by the reader 9, 9a each time the tubes are taken into charge.

Figure 3:
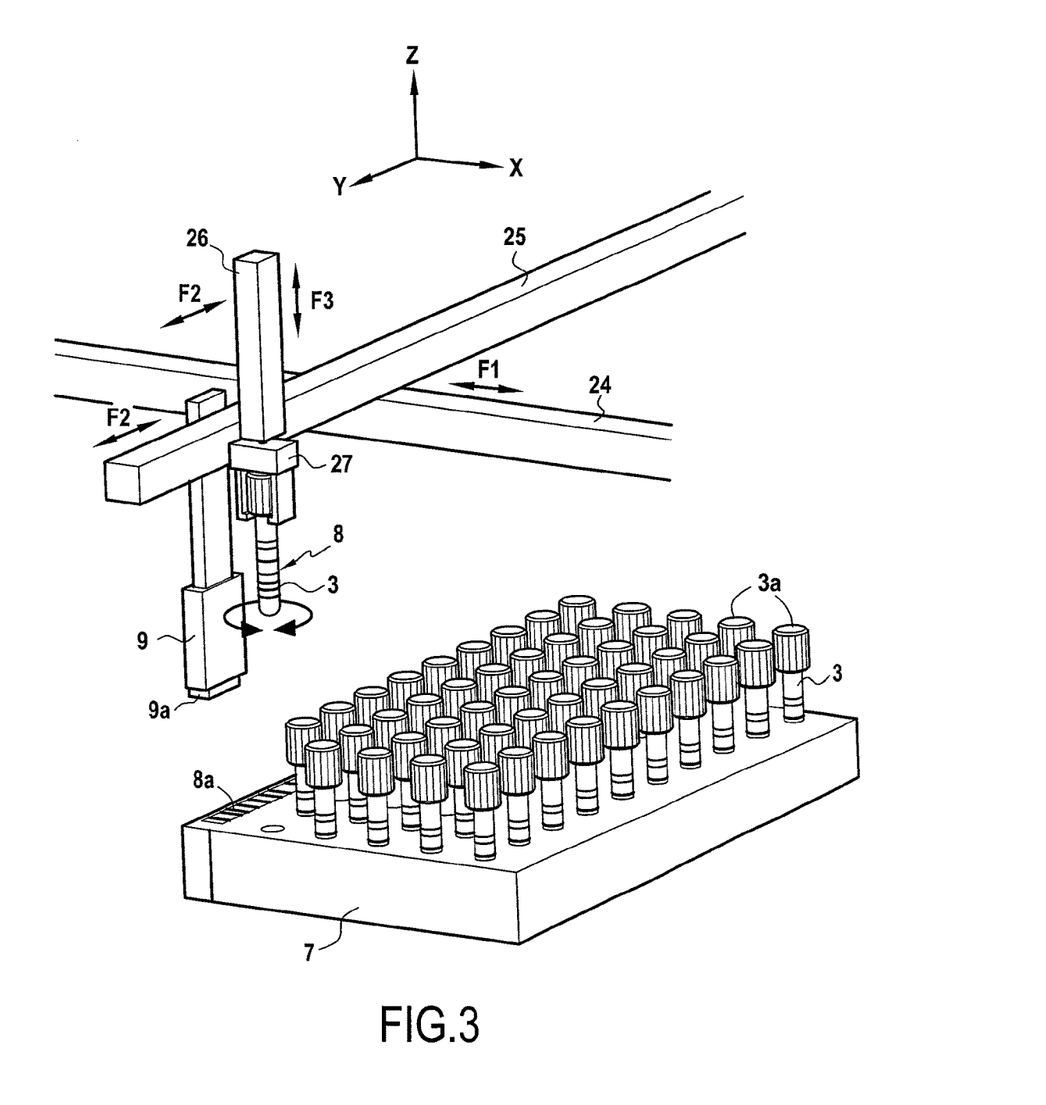
FIG. 3 is a fragmentary view of robotic gripper and displacement means of the device of the invention associated with means for reading bar codes identifying samples.

In an advantageous embodiment, the reader 9 for reading the identification means 8 of the tubes, and the reader 9a for reading the identification means 8a of the racks 7 may be contiguous with each other on a common read device as shown in FIG. 3, thus enabling the identification means 8 of a tube gripped by the clamp 27 and the identification means 8a of the rack 7 from which the tube 3 was taken to be read simultaneously.

In order to prepare blood samples contained in the tubes 3, the device 1 also includes a preparation zone or pre-analysis module 10. Additionally, it also includes a compartment 11 for conserving tubes 19 having control samples of blood, an emergency treatment compartment 12 communicating with the outside of the device through an opening 4c in the enclosure 4 of the device, and at least one access compartment or zone 13a, 13b giving access to an automatic analyzer, whereby the tubes of blood for analysis or the tubes of control samples are made available to the analyzer via two openings 4a, 4b in the enclosure 4 after being prepared for having blood taken therefrom and analyzed.

The disposition of the various zones, modules, or compartments of the device on the work surface 2 can be varied. Nevertheless, it is appropriate to take care to retain a certain degree of proximity between the storage compartment 6, the pre-analysis module 10, and the analyzer access zones 13, 13b giving access to the analyzer, so that the time required for transferring tubes 3 of blood between these elements is minimized, thereby guaranteeing the reliability and the effectiveness with which samples are prepared for analysis and of the analyses performed subsequently thereon.

The pre-analysis module 10 has a plurality of preparation and/or treatment means for acting on the samples of blood for analysis under the control of said automatic controller 5 and used for carrying out automatically a sample preparation sequence that is determined as a function of the information read on said identification means 8 of the tubes 3 and/or of information input into said automatic controller by the operator in charge of analyzing said samples.

During this preparation sequence, operations are performed of verifying and conditioning samples and/or tubes 3 containing them, and in particular agitation of the tubes prior to analysis. It is essential to agitate samples of total blood before any analysis in order to ensure that all of the blood cells are in suspension before being taken by the analyzer.

To this end, the pre-analysis module includes an agitator 14, preferably a rotary agitator, comprising three agitation wheels, each having a housing into which a tube for agitating can be inserted and all mounted on a common rotary shaft, thus enabling three tubes of blood to be agitated simultaneously in the example of FIGS. 1 and 2.

The wheels of the agitator may or not be coupled in rotation, thus making it possible to dissociate rotation of each wheel in the agitator and thereby increase the throughput of the device by enabling tubes of blood to be put into place and taken from a wheel without interrupting agitation of the other wheels.

Nevertheless, it is also possible to perform agitation by partially overturning the tubes or by performing Vortex type agitation with the help of means suitable for turning the tube about its own axis, these modes and means for performing agitation being well known to the person skilled in the art in the field of analyzing blood. Similarly, the number of agitation housings may be selected, like the capacity of the storage compartment, as a function of the rate at which analyses are to be performed.

The pre-analysis module also includes a device 15 for aerating said tubes, comprising a needle for piercing the plug of the tube so as to eliminate any residual pressure or suction in the tube so as to enable the analyzer to take blood properly from the tube.

In addition, it is also advantageous to associate the agitator 14 and the tube aerator device 15 with a device 16 for detecting the level of blood in the tubes and the presence of any clots in the blood, such as an optical detector provided with means for transmitting and receiving light rays, for example. Preferably, the pre-analysis module also includes a device 17 for monitoring the depth to which plugs have been engaged into the tubes, and where appropriate a device 18 for heating said tubes 3 in order to raise certain samples to an analysis temperature that is appropriate for certain blood pathologies, or when said blood samples have been extracted from the refrigerator. Advantageously, the heater means are preferably constituted by thermoelectric cells, e.g. Peltier effect cells, that can thus serve to heat or to cool said samples, depending on the electrical polarity with which they are powered.

The preparation device 1 in accordance with another advantageous characteristic thereof also includes a compartment 11 for storing and conserving tubes 19 containing control samples of blood, i.e. tubes of blood that are used daily for verifying automatic analyzers of total blood, said compartment including means for cooling said tubes. In this compartment 11, which is preferably isolated unlike that which is shown in the figures for reasons of clarity, said tubes 19 containing control samples of blood are positioned and maintained in individual housings of a metal support 20 fitted with thermoelectric cells (Peltier effect cells) in said housings or at the peripheries thereof in order to keep the tubes 19 of control samples of blood cold, thereby ensuring that they are properly conserved over time.

Finally, the preparation device includes a zone or compartment 12 for emergency treatment that can be accessed by an operator from outside the device through an opening 4c in the enclosure of the device 1 without it being necessary to stop the preparation and analysis of the samples of total blood contained in the storage compartment 6.

This emergency treatment compartment 12 is for managing all situations involving emergency analyses or unconventional analyses that normally disturb proper operation of analyzers. This applies, for example, to tubes fitted with plugs that cannot be pierced by the needle of the analyzer, which need to be opened before being made available to the analyzer, or indeed to tubes of a smaller format, as are commonly used for taking blood samples from children, and that require an adapter so as to enable them subsequently to be inserted into the automatic analyzer.

A small-capacity rack 21, having a maximum of about ten housings 22, is placed in said emergency treatment compartment 12 to receive one or more tubes 23 placed directly by hand by the operator in said housings 22 of the rack 21 so that the preparation device takes charge of them individually and on a priority basis over the tubes 3 of blood stored in the storage compartment 6.

The housings 22 can also serve to make available to the operator a tube 3 of blood that was previously placed in the storage compartment 6 and without interrupting the automatic analysis system. The operator can thus very easily and without danger recover a specific tube, e.g. for the purpose of performing additional analyses thereon.

In order to handle the tubes of blood placed on the support 7 in the storage compartment 6 or in the rack 21 of the emergency treatment compartment 12, and in order subsequently to move them individually inside the device towards the preparation and verification means of the pre-analysis module and then to an analyzer via an analyzer access zone, said device advantageously includes robotic gripper and displacement means 24, 25, 26, and 27 controlled by said automatic controller 5.

These means comprise in particular a hinged clamp 27 adapted to grip said tubes 3, 19, 23, preferably under the base of the plug, said clamp 27 being movable vertically and horizontally in translation by a transporter device comprising at least three motor-driven guide rails 24, 25, 26 running along three orthogonal axes X, Y, and Z, and connected together in pairs: a stationary horizontal first rail 24 extending all along the long dimension of the work surface 2 and supporting a second rail 25 that is likewise horizontal and that is perpendicular to said first rail 24. The second rail 25 is movable in translation on said first rail in the directions of double-headed arrow F1, and a vertical third rail 26 is secured to said second rail 25 and is movable in horizontal translation in directions of double-headed arrow F2 thereon and also in vertical translation in the directions of double-headed arrow F3 perpendicularly thereto, said clamp 27 being secured to said third rail 26.

In a preferred variant embodiment shown in detail in FIG. 3, said clamp 27 is mounted to rotate on said third rail 26 so as to be capable of pivoting about a vertical axis parallel to the Z axis. In this configuration, the clamp 27 can grip a tube 3 and enable it to turn about its own axis, which is particularly advantageous in order to read the individual identification means 8 (a bar code in the figures) of each tube placed in the racks 7, 21 of the storage compartment 6 or of the emergency treatment compartment 12 by using a reader 9 that is associated with said rotary clamp 27, as shown in FIG. 3. Rotating the tube makes it possible quickly to find a zone of the identification means that is not masked by the jaws of the clamp 27 so as to read the data and record it in the automatic controller without it being necessary to move the tube along the transporter rails to a stationary reader in a determined position within the device. This achieves a significant saving in time during the stage of initiating preparation of blood samples for analysis.

The operation of the preparation device 1 of the invention is described below, the device being associated for this example with an automatic analyzer 28 identified by a side wall in FIG. 1, said analyzer 28 being connected to the automatic controller 5 of the preparation device 1 and being suitable for communicating therewith a network module (not shown).

After a stage of switching on the analyzer 28 and the preparation device 1, which takes place in the morning before beginning analyses, and during which mechanical and electronic checks are performed on the instrument, together with rinsing and priming liquids and analysis reagents, the automatic controller 5 is used to launch a verification stage, also referred to as a "quality control" stage that is mandatory and that is carried out completely automatically and independently by the preparation device.

As mentioned above, the tubes 19 containing control samples of blood are conserved in the conservation compartment 11 of the preparation device 1. This presents the advantage that the selection of tubes containing control samples of blood and the rules for monitoring and validating that can be set by the user in order to comply the legislation in force in each country or as a function of the laboratory, with this being handled by the preparation device. Automating these tasks makes it possible to comply strictly with the conditions of use that apply to control samples of blood. These conditions relate mainly to the use-by date, storage conditions, the maximum number of times blood can be taken from a tube that has already been used, and conditions relating to raising temperature and to agitation.

During this quality control stage, the robotic clamp 27 selects the tube 19 containing a control sample of blood for analysis from the conservation compartment 11 of the preparation device, and places it in the heater device 18 in order to accelerate its temperature rise, and then in the agitator 14 in order to homogenize the blood contained in the tube. Where appropriate, it is possible to use heating agitators in order to take advantage of the agitation stage for accelerating the heating of the tubes containing control samples of blood.

The tube 19 containing a control sample is subsequently placed by the robotic clamp 27 in a carriage 29*b* in the access zone 13*b* for its introduction into the analyzer 28 where it is analyzed.

Once the tube 19 containing the control sample has been analyzed it is subsequently taken from the analyzer 28 to the preparation device 1 by the carriage 29*b*, and is then returned to its starting location in the conservation compartment 11 by the robotic clamp 27.

To ensure that the verification is performed on an appropriate control sample tube 19, for which the use-by date and the number of prior analyses have not been exceeded, the identification means 8 of the control sample tube 19 are read while the tube is being held by the robotic clamp 27 in order to detect any accidental interchange of control sample tubes 19 in the conservation compartment 11.

The results are subsequently displayed on the monitor screen 5*b* of the automatic controller 5 and recorded and archived therein. This makes it possible to verify automatically the results of analyzing control samples, and if these results lie outside tolerance limits, then it is possible to proceed with a new analysis on the same control sample tube or on a new tube available in the refrigeration conservation compartment, and to continue to do so until correct results are obtained.

After quality control validation, it is possible to proceed with processing the tubes 3 of total blood for analysis. These tubes are placed in racks 7 that have been installed by the operator directly in the storage compartment 6 of the preparation device.

Once the racks 7 have been loaded into the device 1, the operator launches the process of analyzing the samples from the automatic controller 5. Initially, the clamp 27 takes hold of a tube 3 of blood for analysis in a rack 7 in the storage compartment 6, extracts it from its housing, reads the bar code or radiofrequency marker constituting its identification means 8, and transmits the position of the tube in the rack 7 to the automatic controller 5.

Thereafter, the clamp 27 moves the tube 3 from the storage compartment 6 to the pre-analysis module 10 where preparation of the sample begins. The robotic clamp 27 begins by taking the tube 3 to the tube aerator device 15, and then the robotic clamp takes the tube to the optical detector 16 to verify the level of blood in the tube and the possible presence of clots. If the verification is good, then the tube 3 is subsequently taken by the robotic clamp 27 to the station 17 for verifying the depth to which the plug is engaged into the tube. If that is correct, the clamp then places the tube in the agitator 14 so as to enable it to be subjected to a sustained stage of agitation performed in compliance with the recommendations of the National Committee on Clinical Laboratory Standards (NCCLS).

Once the agitation has been completed, and if there is no need to heat the blood prior to analysis, the clamp 27 then extracts the tube of blood for analysis from the agitator 14 and takes it to an analyzer access zone 13*a*, 13*b* where it places the tube 3 in a transporter carriage 29*a*, 29*b* fitted with a support suitable for holding the tube in a position suitable for its entry into the analyzer and for enabling a sufficient quantity of blood to be taken therefrom for analysis. Once the tube has been placed in the carriage, it penetrates into the analyzer through the opening formed for this purpose in the walls separating the enclosure of the preparation device from the analyzer so as to be taken to the station in the analyzer where blood is taken to analyze the sample contained in the tube.

Once blood has been taken from the tube by the analyzer, the carriage then returns to its starting position in the access compartment of the preparation device in which the robot clamp 27 again takes hold of the tube and transports it to its starting location in a rack 7 in the storage compartment.

Depending on selections made by the operator, it is also possible to program the robot clamp 27 so that the tubes of total blood are not replaced in their starting positions after being analyzes, but are taken to another rack 7 that is initially empty in the storage compartment 6 of the preparation device, or indeed the tubes can be sorted as a function of the result of the analysis performed so as to occupy a variety of previously empty racks provided for this purpose in the storage compartment. The tube sorting function is advantageous in particular in that it enables all of the tubes that require additional analyses to be grouped together on a single common rack 7 so as to avoid any need for the operator to perform a manual sorting operation.

For reasons to do with the rate at which analyzes are to be performed in the laboratory, the operations of preparing samples, in particular the agitation thereof, are preferably performed simultaneously on a plurality of tubes as shown in FIG. 1. The automatic controller 5 manages the various movements of the tubes by the robotic clamp 27 so as to optimize the duration of agitation and the waiting time which must be minimum between the end of agitation and analysis.

Still for the purpose of improving the rate of analysis throughput, it is advantageous for the carriages that transport tubes for analysis to have a plurality of housings so as to receive a plurality of tubes for analysis prior to penetrating into the analyzer, so as to anticipate loading of the tubes for analysis a little and allow the robot time to recover the tube returned by the analyzer.

In particular, there is no urgency in recovering an analyzed tube for the purpose of putting it back into place. The rack can thus contain the tube for analysis together with one or more tubes that have already been analyzed. This disposition helps optimize the movements of the clamp and to maintain a high rate of throughput.

The preparation device of the invention also makes it possible to handle circumstances in which an operator needs to perform emergency analyses on tubes 3 of blood that are presented in the storage compartment 6 of the device 1 or on tubes 23 coming from outside and that which were not expected for analysis. This situation is very common, but difficult to manage in a laboratory that is highly automated in which it is necessary to interrupt ongoing analyses in order to pass through the tube(s) that are considered to be urgent.

Using the robotic clamp 27 fitted with an identification reader 9 as shown in FIG. 3, it is particularly easy and quick to find a tube 3 placed in the storage compartment 6 and to process it as a priority and in complete safety without slowing down the rate of throughput of the device and without requiring manual intervention by the operator.

Similarly, if the tube 23 for emergency analysis is not in the storage compartment of the device, the operator can place it in the rack 21 in the emergency treatment compartment 12, and can use the keypad 5*a* or the touch-sensitive screen 5*b* of the automatic controller 5 to program the robotic clamp 27 to take charge of this tube on a priority basis over the tubes situated in the storage compartment 6 so as to perform the analysis urgently on said tubes without breaking the automatic nature of the analysis system.

Thus, the emergency treatment compartment 12 gives privileged access for an operator to perform any exceptional or non-automatible operations, and also to recover a tube 3 that is present inside the device, which the robotic clamp can easily find and place in the rack 21 in the emergency treatment compartment 12.

The preparation device 1 of the invention also enables the installation in analysis laboratories to be made highly modular in combination with different categories of automatic analyzers conventionally used in such laboratories.

Figure 4:
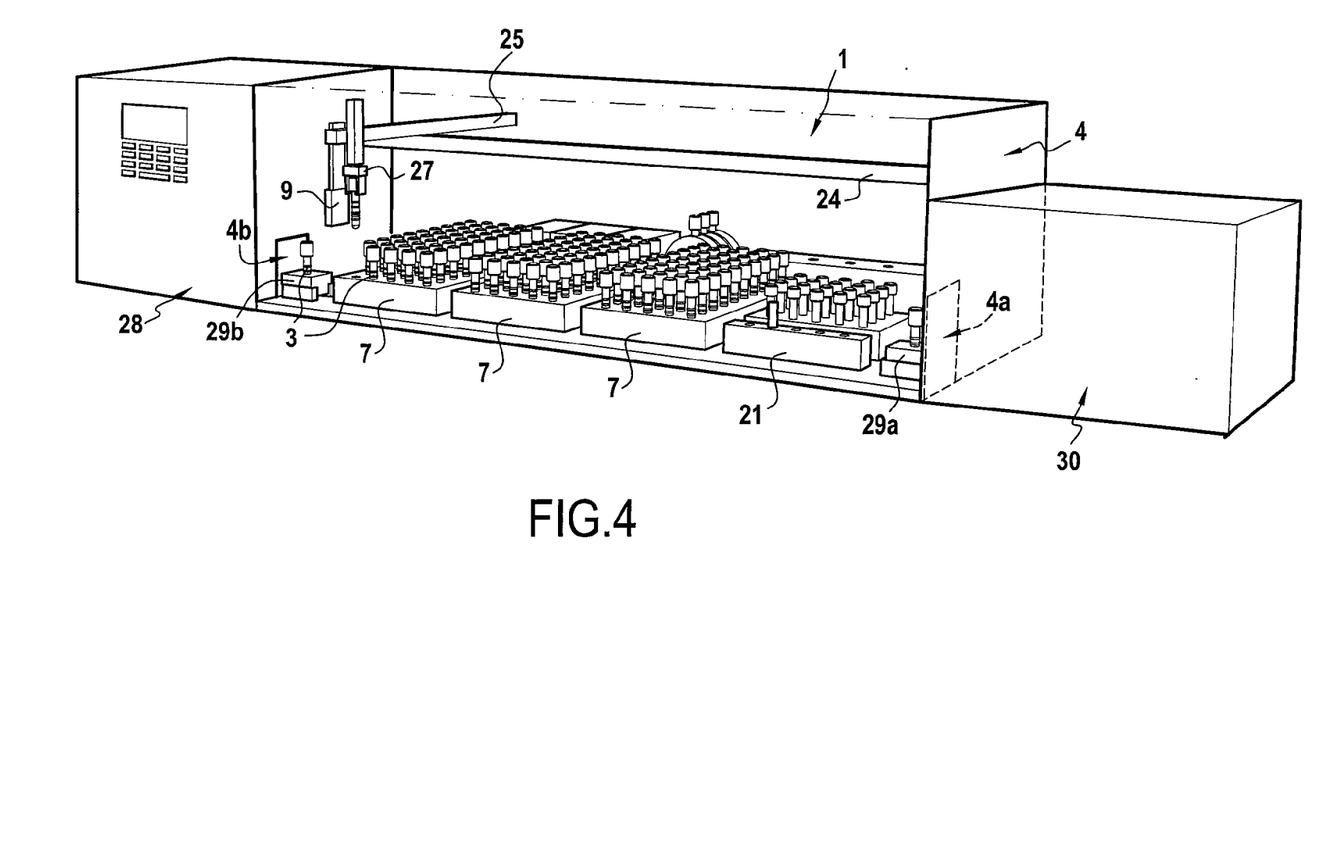
FIG. 4 is a diagram of an automatic analysis device incorporating a device of the invention for preparing analyses co-operating with two automatic analyzers of samples of total blood.

As shown in FIG. 4, it is thus possible to couple the device 1 of the invention with two analyzers 28 and 30. In an application dedicated to hematology, the analyzer 28 is preferably a cell counter, while the analyzer 30 is preferably an automatic machine for making blood smears and specifically for dying the cells of the smear so as to facilitate subsequent observation using a microscope.

In this configuration, the device 1 interposed between the analyzers 28 and 30 serves to position the tube 3 for analysis in the carriage 29*b* of the access zone 13*b* of the analyzer 28 and the tube 3 for providing a blood smear in the carriage 29*a* of the access zone 13*a* of the machine 30.

Since a request for a blood smear is usually associated with the result from the analyzer, it can be seen that this configuration makes it possible to wait for the result from the analyzer before deciding to return the tube 3 to its position in a rack 7 or to place it in the carriage 29*a* for making a smear. Depending on the duration of the analysis and on the availability of the preparation device 1, it might be necessary to mix the blood by positioning the tube 3 on one of the wheels of the agitator 14 prior to placing it on the carriage 29*a* of the machine 30.

Other combinations are possible, and in particular it is possible to couple an analyzer with a different automatic machine that performs analyses on total blood useful in diagnosing a pathology, such as C-reactive protein (CRP) assay, or measuring sedimentation rate.

What is claimed is:

1. A method of preparing analyses of samples of total blood, the samples being conserved in tubes including identification information relating to the sample contained in the tube for identifying the samples and closed by plugs, the method being characterized by the following successive steps:
   a) placing a tube in a storage zone and reading the identification information of the tube by a reader as soon as the tube is placed in the storage zone, such that the information read from the identification information may be recorded in an automatic controller in order to know the identity of the patient, the type of analysis to be performed on the sample of total blood contained in the tube, and to determine automatically therefrom the type of preparation to which each tube is to be subjected to before analysis, the information being recorded together in relation with the positions of the tubes so as to establish a programmed electronic map of the tubes in the storage zone prior to proceeding with the following steps b) to f);
   b) selecting, using the programmed electronic map, a tube in the storage zone for processing,
   c) taking and moving the selected tube individually with the help of a robotic gripper controlled by the automatic controller, from the storage zone to at least one preparation zone for preparing the tube and the total blood sample, wherein the tubes are not moved collectively in the storage zone;
   d) preparing the selected tube and the sample in the preparation zone in application of a preparation sequence that is determined as a function of the information read from the sample identification information and/or information input into the automatic controller by an operator, the sequence not using any reagent and including at least agitating the tube so as to mix together all of the components of the total blood contained therein;
   e) individually displacing the selected tube immediately after preparation with the help of the robotic gripper to at least one access zone giving access to an automatic analyzer of total blood to analyze the total blood sample contained in the tube as a function of the information read from said identification information of the tube;

f) extracting the selected tube from the analyzer from the access zone after analysis and replacing it in the storage zone with the help of the robotic gripper; and g) reiterating operations b) to f) for the other samples, wherein steps b) to f) are performed for an individual sample tube without using a cassette.

2. A method according to claim 1, wherein in step a) the tubes are placed and held vertically in supports, each having a plurality of individual housings of format suitable for receiving a tube and organized in rows of adjacent housings, the supports being positioned in the storage zone suitable for receiving a plurality of the supports and accessible to the robotic gripper.

3. A method according to claim 1, wherein in step d), at least one of the following additional operations is performed:

causing the tube to be aerated; and
verifying the level of the sample of total blood in the tube; and
determining whether any blood clots exist in the sample; and
verifying the depth to which the plug closing the tube has been engaged in the tube.

4. A method according to claim 3, wherein in step d) the temperature of the sample is set, preferably by heating.

5. A method according to claim 1, wherein in step a) a tube is placed in an emergency treatment zone and the automatic controller is programmed so that the preparation and analysis of the tube is performed with priority over that of the tube(s) present in the storage zone.

6. A method according to claim 2, wherein in step f), the tubes are sorted and stored in different supports with the help of the robotic gripper as a function of the results of the analyses performed on the samples contained in the tubes and/or as a function of any additional operations that are to be performed on the samples.

7. A method according to claim 1, wherein prior to preparing and analyzing the samples of total blood, quality control is performed using tubes containing control samples of total blood, the control sample tubes being conserved in a refrigerated conservation zone accessible to the robotic gripper, the control sample tubes being heated and prepared like tubes of unknown total blood, and then successively introduced into the analyzer and recovered automatically in order to be replaced in their starting locations in the refrigerated zone by the robotic gripper.

8. A method according to claim 7, wherein the analysis of at least one control sample tube is prepared periodically after preparing and analyzing a determined number of total blood tubes in the analyzer, the control sample tube being taken, prepared, and introduced into the analyzer and then recovered and stored by the robotic gripper.

9. A method according to claim 7, characterized by the following steps:

taking an average of each of the parameters analyzed on a series of a determined number of unknown total blood samples; and
comparing the average values of the analyzed parameters with ranges of nominal values for the parameters corresponding to healthy patients and recorded in the controller; and
if one of the mean values lies outside the range of nominal values for the corresponding parameter, preparing a control sample of total blood and analyzing the same parameter on the control sample; and
if the value of the parameter as analyzed on the control sample lies in a range of nominal values for the parameter, continuing analysis on a new series of unknown total blood samples, the mean value(s) situated outside the range(s) of corresponding nominal values indicating that at least one sample of pathological blood is present in the preceding series; and
if the value of the parameter analyzed on the control sample lies outside the range of nominal values for the parameter, then the analyzer is calibrated prior to analyzing a new series of unknown total blood samples.

10. A device suitable for preparing analyses of samples of total blood, the device being configured to implement a method according to claim 1, the samples being conserved in tubes each having identification information relating to the sample contained in the tube for identifying the tube and being closed by a plug, the device comprising:

at least one compartment constituting a storage zone for storing the tubes before and after analysis;
at least one reader for reading the identification information of the tubes as soon as the tube is placed in the storage zone and recording the information in an automatic controller in order to know the identity of the patient, the type of analysis to be performed on the sample of blood contained in the tube, and to determine automatically therefrom the type of preparation to which each tube is to subjected before analysis, the information being recorded together in relation with the positions of the tubes so as to establish and program an electronic map of the tubes in the storage zone;
a sorter for sorting tubes before and/or after analyses in the storage zone;
at least one preparation zone for preparing the total blood samples prior to analysis and including at least one treatment device including at least one agitator for agitating the tubes the preparation zone being devoid of any use of reagent and of an incubation chamber;
at least one access zone giving access to at least one automatic analyzer of total blood, the access zone enabling a tube to be placed in the analyzer;
a robotic gripper controlled by an automatic controller, using the programmed electronic map, and suitable for taking hold of and replacing the tubes individually in the storage zone and for conveying them in at least three directions XYZ between the storage zone without using a cassette, the preparation zone and for transferring tubes in the access zone giving access to the analyzer immediately after preparation, the analyzer preferably being connected to and/or controlled by the automatic controller, wherein the tubes are not moved collectively in the storage zone.

11. A device according to claim 10, including supports including individual housings in which the tubes are placed by an operator, the supports being positioned in the storage zone and being manually removable therefrom, the storage zone being suitable for receiving a plurality of supports and being accessible by the robotic gripper so as to enable the tubes containing the samples of total blood for analysis to be taken therefrom and replaced therein.

12. A device according to claim 10, including an emergency treatment compartment that is manually accessible to an operator from outside the device, the emergency treatment compartment also being accessible to the robotic gripper and including at least one tube support element including at least one housing suitable for receiving a tube of total blood.

13. A device according to claim 10, wherein the treatment device further includes an aerator for aerating the tubes.

14. A device according to claim 10, including a compartment for storing and conserving tubes of control samples of total blood to enable the analyzers to be verified, the compartment including a cooler for cooling the tubes.

15. A device according to claim 10, wherein the control sample tubes are positioned and held in the conservation compartment in individual housings of a support, the cooler being constituted by thermoelectric cells preferably placed in the housings or at the periphery thereof.

16. A device according to claim 10, wherein the at least one treatment device further includes at least one of a selection of:
   a detector for detecting the level of total blood in a tube and the presence of clots, if any, in the total blood; and/or
   a detector for verifying the level to which the plug is put into a tube of total blood; and/or
   a heater for heating the tubes, preferably constituted by thermoelectrical cells.

17. A device according to claim 10, wherein the robotic gripper comprises a hinged clamp adapted to take hold of the tubes, preferably under the base of the plug, the clamp being movable vertically and horizontally in translation along three orthogonal XYZ axes by means of a transporter device having at least three guide rails directed along the XYZ axes and connected together in pairs, comprising a first rail that is horizontal and stationary, supporting a second rail that is horizontal and perpendicular to the first rail, being movable in translation thereon, and a third rail that is vertical, being secured to the second rail and being movable in translation thereon and perpendicularly thereto, the clamp being secured to the third rail.

18. A device according to claim 10, wherein the robotic gripper comprises an articulated arm provided at one of its ends with a clamp for gripping the tubes of total blood.

19. A device according to claim 10, the device being confined in a protective enclosure including at least one access opening giving access to at least one analyzer, and a second access opening giving access to an emergency treatment compartment.

20. A device according to claim 10, wherein the access zone(s) giving access to the analyzer(s) includes respective moving carriages suitable for moving between the device and the analyzer, each carriage being controlled by the automatic controller and including at least one housing suitable for receiving a tube of total blood from the robotic gripper.

21. A device according to claim 17, wherein the robotic gripper includes a detector for detecting and/or viewing the tubes containing the samples of total blood and the tubes containing control samples in the storage zones, the preparation zone, the zone(s) giving access to the analyzer(s), in the emergency treatment compartment, and in the compartment for storing and conserving tubes of control samples.

22. A device according to claim 11, wherein the supports disposed in the storage zone and/or in the compartment for conserving tubes of control samples also include identification information suitable for being read by the read means.

23. An automatic device for analyzing total blood comprising at least one automatic analyzer of total blood, the analyzer including a needle for taking total blood from a sample to be analyzed that is contained in a tube, which tube is preferably hermetically closed by a plug, the device including at least one device suitable for preparing analyses of samples of total blood according to claim 10 coupled to the analyzer and communicating therewith via at least one access zone of the preparation device giving access to the analyzer.

24. A method of preparing analyses of samples of total blood, the samples being conserved in tubes including identification information relating to the sample contained in the tube for identifying the samples and preferably hermetically closed by plugs, the method being characterized by the following successive steps:
   a) placing a tube in a storage zone, and reading the identification information of the tube by of a reader as soon as the tube is placed in the storage zone, such that the information read from the identification information may be recorded in an automatic controller in order to know the identity of the patient, the type of analysis to be performed on the sample of blood contained in the tube, and to determine automatically therefrom the type of preparation to which each tube is to subjected before analysis, the information being recorded together in relation with the positions of the tubes so as to establish a programmed electronic map of the tubes in the storage zone prior to proceeding with the following steps b) to e);
   b) selecting, using the programmed electronic map, a tube in the storage zone for processing,
   c) taking and moving the selected tube individually with the help of a robotic gripper controlled by the automatic controller, from the storage zone to at least one preparation zone for preparing the tube and the blood sample, wherein the tubes are not moved collectively in the storage zone;
   d) preparing the selected tube and the sample in the preparation zone in application of a preparation sequence that is determined as a function of the information read from the sample identification information and/or information input into the automatic controller by an operator, the sequence including agitating the tube so as to mix together all of the components of the blood contained therein and at least one of the following additional preparation operations:
      causing aeration of the tube;
      verifying the level of the sample of blood in the tube;
      determining whether any clots exist in the sample contained in the tube;
      verifying the depth to which the plug closing the tube has been engaged; and
      bringing the sample to temperature;
   e) individually displacing the selected tube immediately after preparation with the help of the robotic gripper to at least one access zone giving access to an automatic analyzer of total blood to analyze the blood sample contained in the tube as a function of the information read from the identification information of the tube;
   f) extracting the selected tube from the analyzer from the access zone after analysis and replacing it in the storage zone with the help of the robotic gripper; and
   g) reiterating operations b) to f) for the other samples and wherein steps b) to f) are performed for an individual sample tube without using a cassette.

25. A device suitable for preparing analyses of samples of total blood in accordance with a method according to claim 1, the samples being conserved in tubes each having identification information relating to the sample contained in the tube for identifying the tube and preferably being closed hermetically by a plug, the device comprising:
- at least one compartment constituting a storage zone for storing the tubes before and after analysis;
- at least one reader for reading the identification information of the tubes as soon as the tube is placed in the storage zone in order to record the information read in an automatic controller in order to know the identity of the patient, the type of analysis to be performed on the sample of total blood contained in the tube, and to determine automatically therefrom the type of preparation to which each tube is to be subjected to before analysis, the information being recorded together in relation with the positions of the tubes so as to establish a programmed electronic map of the tubes in the storage zone;
- a sorter for sorting tubes before and/or after analyses in the storage zone;
- at least one preparation zone for preparing the blood samples prior to analysis and including at least one treatment device including one agitator for agitating the tubes, and at least one of the following additional devices:
  - an aerator for aerating the tubes;
  - a detector for detecting the level of blood in the tube and the presence of any clots in the blood;
  - a detector for verifying the level to which the plugs are engaged in the tubes of blood; and
  - a heater for heating the tubes, preferably constituted by thermoelectrical cells; and
- at least one access zone giving access to at least one automatic analyzer of total blood, the access zone enabling a tube to be placed in the analyzer; and
- a robotic gripper controlled by an automatic controller and suitable for taking hold of and replacing the tubes individually in the storage zone, using the programmed electronic map, and for conveying them in at least three directions XYZ between the storage zone without using a cassette, the preparation zone and the access zone giving access to the analyzer, the analyzer preferably being connected to and/or controlled by the automatic controller, wherein the tubes are not moved collectively in the storage zone.

* * * * *